US008028702B2

(12) United States Patent
DaSilva

(10) Patent No.: US 8,028,702 B2
(45) Date of Patent: Oct. 4, 2011

(54) ARM POSITIONING AND SUSPENSION ASSEMBLY

(76) Inventor: Manuel F. DaSilva, East Greenwich, RI (US)

( * ) Notice: Subject to any disclaimer, the term of this patent is extended or adjusted under 35 U.S.C. 154(b) by 268 days.

(21) Appl. No.: 12/130,147

(22) Filed: May 30, 2008

(65) Prior Publication Data

US 2009/0293884 A1 Dec. 3, 2009

(51) Int. Cl.
*A61G 15/00* (2006.01)
*A61F 5/00* (2006.01)

(52) U.S. Cl. ................ 128/845; 5/623; 5/646; 606/241; 606/245; 602/32; 602/33

(58) Field of Classification Search .................... 602/36, 602/32, 33; 128/845, 846, 878; 5/624, 623, 5/651, 646, 648, 649; 606/241, 245; 403/56, 403/76, 90, 114, 115, 122
See application file for complete search history.

(56) References Cited

U.S. PATENT DOCUMENTS

| | | | | |
|---|---|---|---|---|
| 4,616,637 | A | 10/1986 | Caspari et al. | |
| 4,807,618 | A | 2/1989 | Auchinleck et al. | |
| 4,858,903 | A | 8/1989 | Tari et al. | |
| 5,127,898 | A | 7/1992 | McConnelll | |
| 5,419,756 | A | 5/1995 | McConnell | |
| 5,957,135 | A | 9/1999 | Molina | |
| 5,961,512 | A | 10/1999 | Purnell | |
| 6,220,776 | B1 * | 4/2001 | Reeves | 403/102 |
| 6,435,186 | B1 * | 8/2002 | Klemm | 128/845 |
| 6,629,944 | B2 | 10/2003 | Smart | |
| 6,830,552 | B1 * | 12/2004 | Gonzalez | 601/137 |
| 7,131,955 | B2 * | 11/2006 | Price et al. | 602/36 |
| 7,297,128 | B2 | 11/2007 | Binder et al. | |
| 2001/0031937 | A1 | 10/2001 | Repice et al. | |
| 2006/0200061 | A1 | 9/2006 | Warkentine | |
| 2007/0124863 | A1 | 6/2007 | Kirn | |

* cited by examiner

*Primary Examiner* — Patricia Bianco
*Assistant Examiner* — Keri Nelson
(74) *Attorney, Agent, or Firm* — Barlow, Josephs & Holmes, Ltd.

(57) ABSTRACT

An arm support and positioning assembly is provided that includes a vertical member, an engagement member and a horizontal member having one end engaged with the vertical member through a ball joint assembly and the other end affixed with the engagement member through a wedge lock. The engagement member receives and retains a patient's arm support during the surgical or medical procedures. The vertical member is attached to the clamp support assembly affixed with the operating table. The ball joint assembly includes a first hinge plate, a second hinge plate, and a ball joint having an elongated ball neck on one end and a spherical ball on other end. The ball shape end allows the horizontal member to rotate at a varied angular position with respect to the vertical member thereby providing a greater degree of adjustability to the surgeon.

12 Claims, 8 Drawing Sheets

ARM POSITIONING AND SUSPENSION ASSEMBLY

BACKGROUND OF THE INVENTION

The present invention relates generally to a limb support and positioning structure used for maintaining a patient's arm in the desired position for surgery thereon. More specifically, the present invention relates to a surgical limb support and positioning structure that allows for the adjustable positioning of the patient's arm during the implementation of a surgical procedure.

Limb support and positioning devices, also referred to as traction devices, are commonly used by surgeons to maintain a patient's limb or extremity in a controlled and elevated position during a surgical procedure. For example, if a person has a broken arm, a traction device may be employed to elevate the arm while the person is reclining on an operating table in order to immobilize and align the arm so that the fracture can be repaired properly. In this regard, numerous devices and structures are currently available in the prior art that are tailored for use as support structures for a limb or the limbs of a patient and particularly for use during the implementation of surgical procedures where it is of extreme importance that the limb or limbs being operated on are immobilized in a desired position in order to insure proper alignment during the procedure.

The difficulty with a great number of the prior art devices is that they are tailored to a shape that provides positioning for only a single procedure and are therefore not useful in other contexts. Further, because of their specialized nature, such devices often do not include any adjustability for the positioning of the limb retained therein. Such devices take the form of bolsters and arm boards that are designed to constrain the forearm of the patient while a medical device is applied to the patient's arm. In these devices there is some degree of adjustability relative to the longitudinal extension of the support and some minor adjustability for supporting the hand. However, the degree of angular adjustment in supporting the forearm, elbow, arm and shoulder is only of relatively limited nature.

In one prior art device, an assembly is provided that is mounted in a stand on the floor or on the base of the surgical table. A supporting rod extends upwardly from beneath the table and supports a secondary member using an articulated joint that in turn engages the patient's hand or forearm in order to support and position the limb. In operation however, the primary support bar is positioned such that it is often in the way of accessing the patient's elbow, requiring instead that the surgeon work around the bar. Further, when the patient is in a supine position and the elbow is in an extended position the bar of the support must be fully extended wherein it hits the patient's body, thereby limiting the overall total extension that is possible. In another prior art device, a rope weight design is used in positioning the patient's arm. However, since the device is applied in a non-sterile fashion, the surgeon is limited in the intraoperative adjustments that can be achieved.

Therefore, although a variety of traction assemblies are known in a prior art, there still exit a need to provide an arm support assembly that can better position a patient's arm during a surgical process. There is a further need for an arm positioning apparatus that can fully sterilized and that allows fully adjustable support of a patient's arm in a manner that facilitates better positioning and support of the shoulder arm and elbow joint while allowing unimpeded access thereto.

BRIEF SUMMARY OF THE INVENTION

In this regard, it is an object of the present invention to provide an arm support assembly configured to provide varied angular arrangement facilitating the patient's arm positioning and support during a surgical process. To achieve the aforementioned objective and to overcome the drawbacks of the prior art, the present invention discloses a surgical limb support and positioning structure. More specifically, the present invention discloses an arm support assembly that is configured to provide a varied angular adjustment allowing greater flexibility to the surgeon. In addition, the present invention facilitates further angular adjustment in a transverse direction and pivotal positioning relative to a horizontal plane so as to impart a varied angular adjustability to the arm support assembly.

The arm support assembly of the present invention generally includes a vertical member, an engagement member and a horizontal member having one end engaged with the vertical member and the other end affixed with the engagement member. The engagement member has a quick release fitting on one end thereof that is configured to receive and retain a patient's arm or a hand splint support during the surgical or medical procedures. The arm support assembly of the present invention is configured to affix into a clamp assembly, engaging with the accessory rails of a surgical or operating table, such as the clamp assembly disclosed in the present applicant's co-pending U.S. Utility patent application Ser. No. 12/037,965, filed Feb. 27, 2008, the contents of which are incorporated herein by reference.

The vertical member is inserted into the sterile operating table clamp assembly. The vertical member thereby provides a mean for engaging the arm support assembly with the operating table and also provides a desirable height for the arm support assembly during the surgical procedure. The horizontal member includes a tube member and a shaft member. The shaft member connects the horizontal member with an engagement member through a wedge lock and the tube member is connected to a ball joint assembly The ball joint assembly includes a first hinge plate, a second hinge plate and a ball joint having an elongated ball neck on one end and a spherical ball on other end. The first and second hinge plates are pivotally fixed relative to one another using a plurality of screws on one side and are clamped using a releasable clamping member on the other side. The ball shaped end is disposed between the first and the second hinged plates and the ball neck is extended outward from the first hinge plate. The first hinge plate includes an aperture to receive the spherical ball shape end with the neck extending therethrough and the second hinge plate having a depression on a surface adjacent to the first hinge plate to retain and tighten against the spherical ball end. Further, the second hinge plate is connected to the socket that receives the vertical member. The ball shape end allows the horizontal member to rotate at a varied angular position with respect to the vertical member thereby providing a greater degree of adjustability to the surgeon. When the surgeon determines the desired position intraoperatively, the patient's arm support in the desired position is secured by a quick release fitting of the arm support assembly.

Further, the horizontal member is configured to have an adjustable length through the shaft member. The shaft member is inserted into the tube member by a telescopic mechanism thereby providing varied length to the horizontal member. Further, a safety knob is provided to fix the tube member over the shaft member. The horizontal member is connected with the engagement member through a wedge lock. The wedge lock allows the engagement member to be rotated along the plane of the horizontal member. Further, the engagement member is configured to provide a quick release fitting that receives and retains a stud of an arm support.

In one embodiment, the quick release socket of the engagement member is configured to receive and retain a sterile wraparound hand splint. The wraparound hand splint is made of a foam material and a metal insert having a stud to affix with the quick release fitting. The wraparound hand splint includes a support frame having a longitudinal member aligned with the axis of the patient's forearm and a transverse member that wraps around the patient's wrist. The support frame is wrapped in a soft material. The stud is provided on the back surface of the wraparound hand splint to affix with the quick release fitting emerging from the engagement member. The wraparound hand splint includes a central member and first, second, third, fourth and fifth panel members extending outward from the central member. Each of the panels is provided with a fastener on their distal ends to wrap the panel around the patient's hand. Further, the third, fourth and fifth panels are provided with the fastener on the patient's hand contacting surface and the fastener on the first and the second panels are complementary to each other.

First, the volar side of the patient's hand in a relaxed fist position is laid on the central member of the wraparound hand splint. The patient's hand is positioned such that the forearm of the patient is substantially coterminous with the central member. The first panel is then folded around the wrist and forearm, and then the second panel is folded over the first panel so that the fastener on the first panel is conformed to engage with the fastener of second panel. Following the engagement of the first and second panel, the top panel is disposed over the patient's hand in a relaxed fist position. Subsequently, the fourth and fifth panels are wrapped around the wrist of the patient's hand and finally the wraparound hand splint is attached to the engagement member of the arm support assembly using the stud.

Various kinds of fasteners, such as hook and loop fastener material for example, are available and are known to a person of ordinary skill in the art can be applied on the panels. Further, a hook and loop type fastening means can be used to tighten the panel members around the patient hand or wrist.

These together with other objects of the invention, along with various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention.

DETAILED DESCRIPTION OF THE INVENTION

The present invention will now be described with reference to the accompanying drawings. The drawings are being used to illustrate the inventive concept and do not intend to limit the invention to the embodiments shown in them.

Figure 1A:
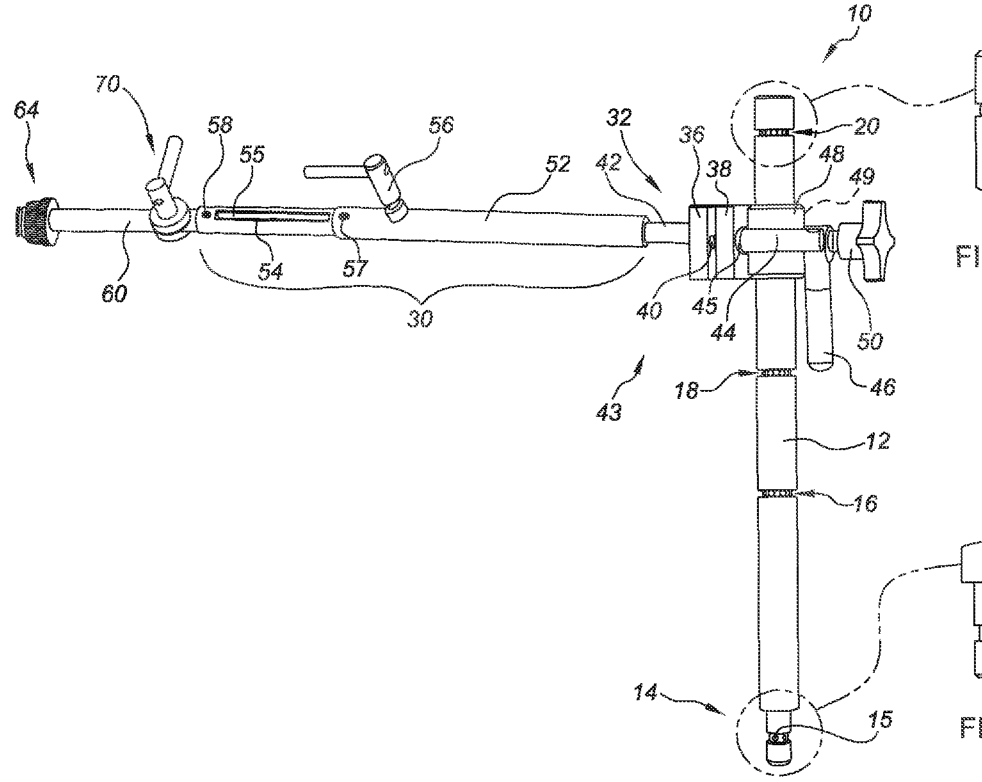
FIG. 1*a* illustrates a perspective view of an arm support assembly of the present invention.

Referring to FIG. 1*a*, a perspective view of an arm support assembly of the present invention is represented. The arm support assembly (10) includes a vertical member (12), an engagement member (60), and a horizontal member (30) having one end engaged with the vertical member (12) and the other end affixed with the engagement member (60). The engagement member (60) is configured to receive and retain a wraparound hand splint for supporting the patient's arm during the surgical or medical procedures. The arm support assembly (10) of the present invention is configured to insert into a clamp operating table assembly, such as the clamp assembly disclosed in the present applicant's co-pending U.S. Utility patent application Ser. No. 12/037,965, filed Feb. 27, 2008, the contents of which are incorporated herein by reference. In an assembled configuration, the arm support assembly is positioned on the clamp assembly through openings thereon and tightened using the locking knob provided on the clamp assembly.

As shown in FIG. 1*a*, the horizontal member (30) includes a tube member (52) and a shaft member (54). The shaft member (54) is inserted into the tube member (52) through a telescopic mechanism thereby providing a varied length to the horizontal member (30). Further, the shaft member includes a groove (55) along its longitudinal length thereby providing a means to affix with the tube member (52) and a wedge lock (70). The tube member (52) at one end is affixed with the shaft member (54) and the other end is connected with a ball joint assembly (32).

Still referring to FIG. 1*a*, the ball joint assembly (32) is moved along the vertical length of the vertical member (12) thereby enabling the arm support assembly (10) to attain the desired height. Once ball joint assembly (32) attains the desired height, the ball joint assembly (32) can be fixed with the vertical member by using a locking knob (50) and a spring-biased retaining pin (49).

Figure 1B:
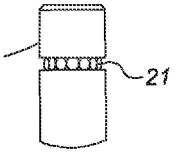
FIG. 1*b* illustrates a detail view of the vertical member's hinge region.
Figure 1C:
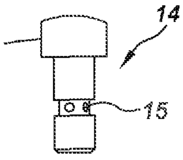
FIG. 1*c* illustrates a detail view of the vertical member's groove region.

The vertical member having a plurality of hinges (16, 18, 20) and a lower end (14) to insert into the operating room clamp assembly (not shown). FIGS. 1*b* and 1*c* illustrate the detailed view of the hinge region (16,18, 20) and the lower end (14) of the vertical member (12). The plurality of hinges (16, 18, 20) having pin holds (21) into which the spring loaded pin (49) is engaged, thereby preventing rotation of the ball joint assembly (32) around the vertical axis of the vertical member. Further, the lower end (14) of the vertical member (12) is provided with a rotational index (15) to affix with the operating room clamp assembly (not shown). The lower member of the operating room clamp assembly (not shown) is provided with an opening to receive the vertical member (12) and a threaded knob to engage with the rotational index (15) thereby preventing rotation of the vertical member (12) around the operating table clamp assembly.

Figure 2:
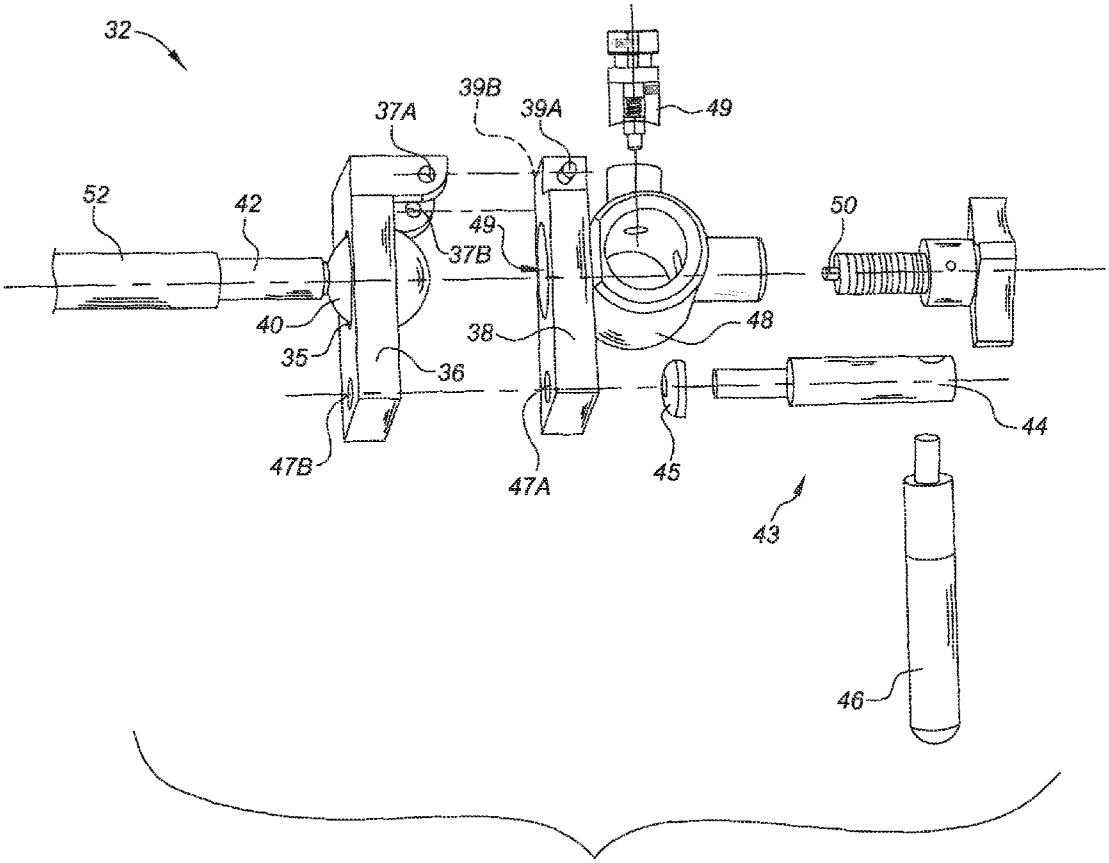
FIG. 2 illustrates an exploded view of a ball joint assembly.

FIG. 2 illustrates an exploded view of the ball joint assembly (32) of the arm support assembly illustrated in FIG. 1*a*. The ball joint assembly (32) includes a pair of hinge plate (36, 38) and a ball joint having an elongated ball neck (42) at one end and a spherical ball (40) at the other. The ball end (40) is disposed between a pair of hinge plates (36, 38), and the ball neck (42) is connected with the tube member (52). The pair of hinge plates includes a first plate (36), having an opening (35) to receive the ball end (40) of the ball joint, and a second plate (38), connected to the socket (48), to receive the vertical member (12). The socket (48) allows the ball joint assembly (32) to rotate around the axis of the vertical member (12) thereby providing flexibility to the surgeon to conform the arm assembly (10) at a desired angular position. Further, the ball joint assembly (32) is movable along the height of the vertical member (12) allowing to position the arm assembly at a desired height thereby allowing the arm support assembly to attain larger degree of flexibility.

The ball joint assembly (32) is provided with a locking knob (50) and a spring biased retaining pin (49) to fix with the vertical member (12) at the desired height and rotational axis of the vertical member (14). In an assembled configuration, the locking knob (50) is locked into pin holds (21) of the hinge region of the vertical member (12). Furthermore, the spring biased retaining pin (49) prevents vertical displacement of the ball joint assembly (32) around the vertical member (12). As shown in FIG. 2, the first (36) and second hinge plates (38) are pivotally fixed relative to one another. Further, the first hinge plate (36) is provided with a plurality of openings (37A, 37B) on a side edge and the second hinged plate (38) is provided with corresponding pins (39A, 39B) on a side edge to pivotally affix the second hinge plate (38) and the first hinge plate (36). The ball shape end (40) is disposed between the first hinged plate (36) and the second hinged plates (38), and the ball neck (42) is extended outward from the first hinge plate (36). The first hinge plate (36) having an aperture (35) that receives the spherical ball shape end (40). Further, the second hinge plate is connected to the socket (48) to receive the vertical member (12). As shown in FIG. 2, the ball shape end (40) allows the horizontal member (30) to rotate at a varied angular position with respect to the vertical member (12) thereby providing a greater degree of adjustability to the surgeon.

The first and second hinge (36, 38) plates are clamped together by a releasable knob (43). The releasable knob (43) includes a clamp pin (44), an eccentric washer (45) and a handle (46). The first and second hinge plates (36, 38) are also provided with openings (47A, 47B) on the front surface to receive the clamp pin (44). Rotation of the handle (46) in turn results in the shaft member (44) to pierce through the eccentric washer (45), through the opening (47A) and then finally received into the opening (47B) of the first plate (36). Further, the eccentric washer (45) acts as a lever as it is compressed between the handle (46) and the first plate (36) creating greater compression between the hinge plate (38) and the clamp pin (44) thereby enhancing the holding strength of the ball joint. Once the clamp pin (44) is tightened, the hinge plates (36, 38) exert pressure on the ball joint thereby reliably retaining the horizontal arm (30) in the desired position.

Referring back to FIG. 1*a*, the horizontal member (30) is configured to have an adjustable length through the shaft member (54). The shaft member (54) is inserted into the tube member (52) by a telescopic mechanism thereby providing varied length to the horizontal member (30). The shaft member includes a groove (55) along its longitudinal length. The groove (55) prevents rotation of the shaft member (54) once it is connected with the tube member (52) and the wedge lock (70). The shaft member (54) at one end is affixed with the tube member (52) using colored markers (57, 58) in order to correctly align the groove with the safety knob (56). Further, a safety knob (56) is provided to fix the tube member (52) over the shaft member (54). When the safety knob (56) is partially engaged onto the groove (55), it prevents rotational displacement but allows horizontal movement of the shaft member (54) inside the tube member(52). When the safety knob (56) is fully engaged onto the groove (55), it prevents rotational and horizontal displacement of the shaft member (54) inside the tube member (52).

Figure 3A:
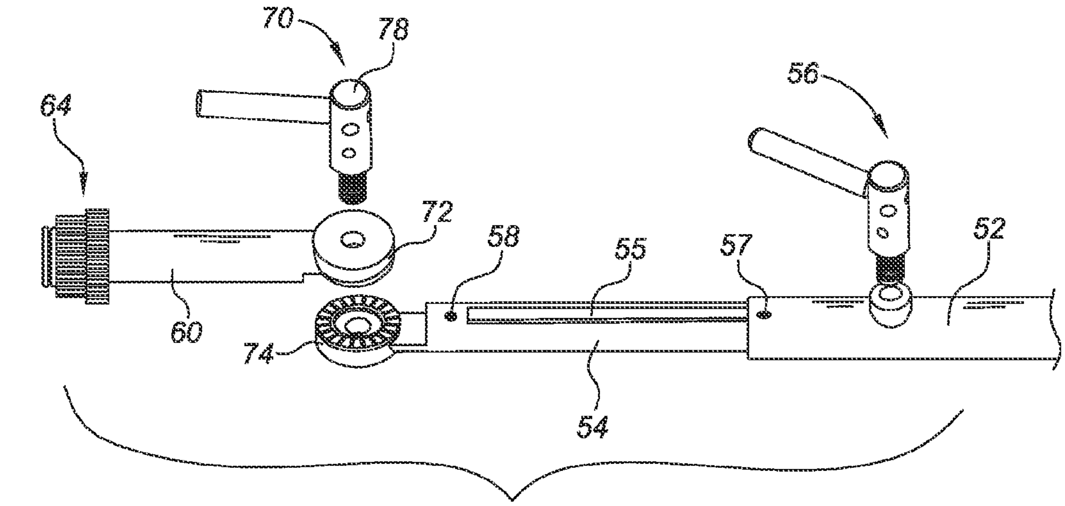
FIG. 3*a* illustrates an exploded view of a wedge lock connecting the engagement member and horizontal member.
Figure 3B:
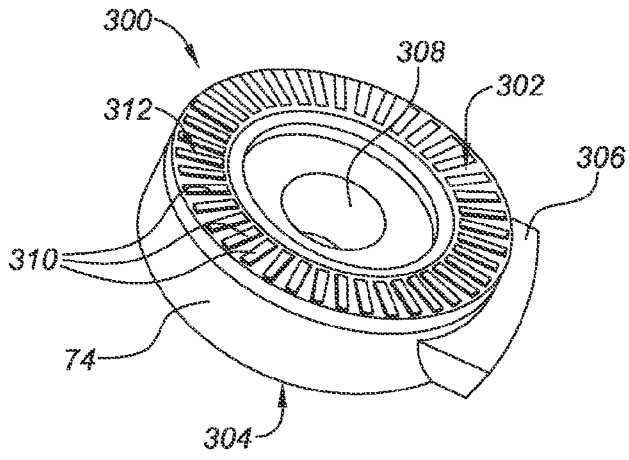
FIG. 3*b* illustrates a perspective view of a plate of the wedge lock represented in FIG. 3*a;*

Referring now to FIG. 3*a*, an exploded view of a wedge lock (70), engaging with the engagement member and the shaft member, is illustrated. The wedge lock (70) includes a top plate (72), a bottom plate (74), and a locking pin (78) to tighten the top and bottom plates (72, 74). The wedge lock (70) allows the engagement member (60) to rotate along the plane of the shaft member (54). FIG. 3*b* shows a perspective view of the bottom plate of the wedge lock illustrated in FIG. 3*a*. The bottom plate (74) includes a top surface (302), a bottom surface (304), a connecting member (306) and an opening (308) in the centre to receive the locking pin (not shown). The top surface (302) of the wedge plate (300) includes a plurality of protrusions (310) to provide an emboss pattern of gear (312). Further, the top plate (72) of the wedge lock (64) is provided with a corresponding emboss pattern of gear on its top surface. The emboss pattern of gears imprinted on the top surface of the corresponding top and bottom plates are complementary to each other. The complementary emboss pattern of gear on the top and bottom plates (72, 74) permeates fastening of the wedge plates thereby providing a locking grip to engage the top and bottom plates.

As shown in FIG. 3*b*, the wedge lock plate includes a connecting member (306) to affix the bottom plate (74) with the shaft member (not shown) or the engagement member (not shown). In an embodiment, shown in FIG. 3*a*, the top plate (72) is connected with the engagement member (60) and the bottom plate (74) is attached to the shaft member (54). Alternatively, the top plate can be connected to the shaft member and the bottom plate can be connected to the engagement member.

As shown in FIG. 3*a*, the wedge lock (70) allows the engagement member (60) to move in its plane thereby providing the engagement member (60) to attain different angular positions. The engagement member (60) is rotated at a desired angle relative to the shaft member (54), the locking pin (78) is used to fix relative angular position of the engagement member (60) and the shaft member (54). The different angular positions of the engagement member (60) provide further flexibility to the surgeon in orienting the patient's arm at a desired position.

Figure 4:
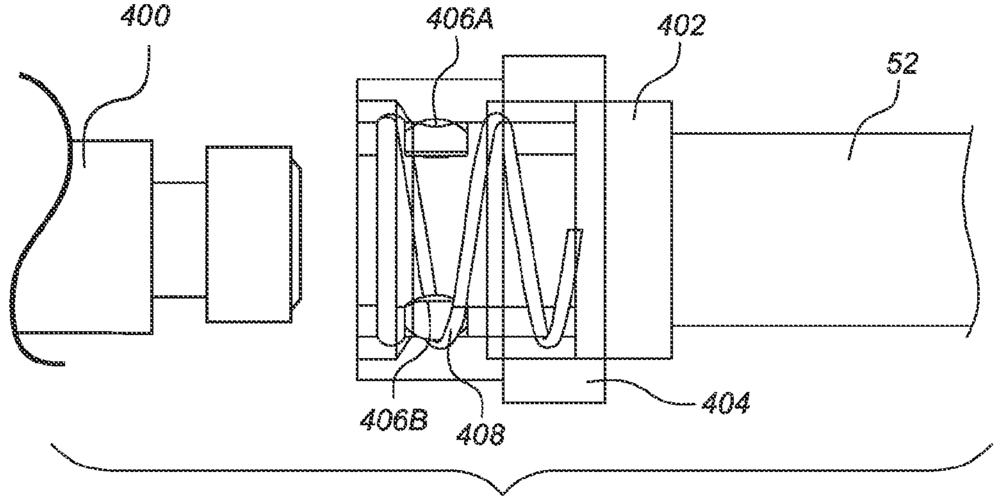
FIG. 4 illustrates a cross sectional view of the quick release fitting according to an embodiment of the present invention.

Referring to FIG. 4, the cross sectional view of the quick release fitting is illustrated. The quick release (64) includes a fixing member (402) to receive a stud (400) emerging out from a wraparound hand splint (not shown), and a sliding member (404). The fixing member (402) includes a pair of ball bearings (406A, 406B) and a spring (408) wrapped on its surface. The spring (408) allows the easy turning in and turning out of the stud into the fixing member (402). In order to affix the wraparound hand splint with the quick release fitting, the stud (400) of the wraparound hand splint is inserted into the fixing member (402). Subsequently, stud (400) exerts upward pressure onto the ball bearing (406A, 406B) thereby providing frictional force to fix its position within the fixing member (402). Further, the sliding member (404) is configured to exert constant downward pressure on the ball bearings (406A, 406B) and prevents upward movement of the ball bearings (406A, 406B) thereby maintaining position of the stud (400) within the fixing member (402).

Figure 5A:
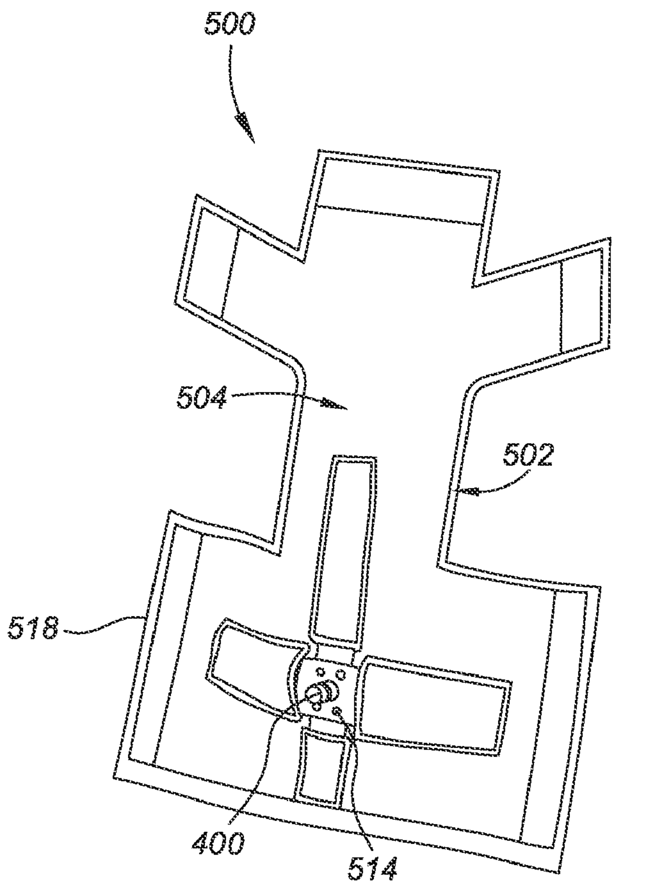
FIG. 5*a* illustrates a rear perspective view of a wraparound hand splint according to an embodiment of the present invention.
Figure 5B:
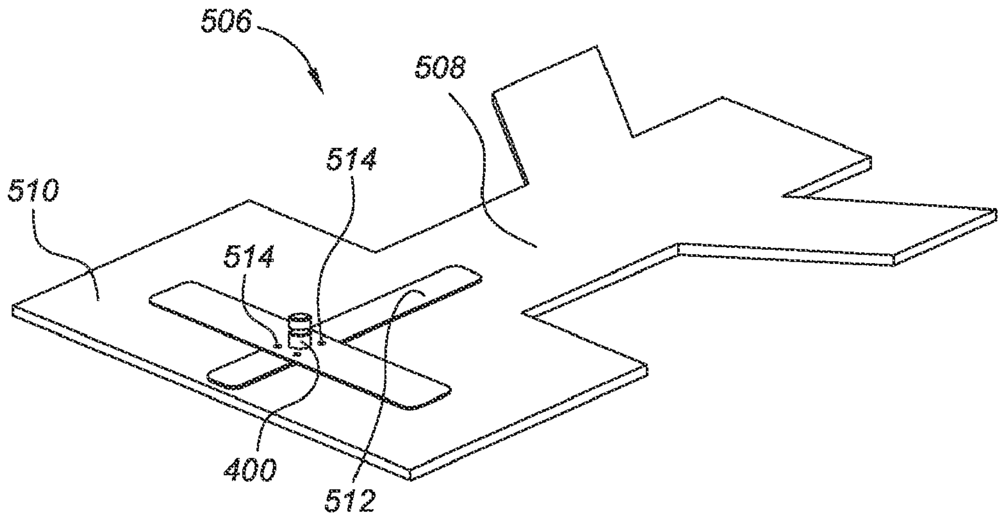
FIG. 5*b* illustrates a perspective view of a support frame of the wraparound hand splint of FIG. 5*a;*

Referring to FIG. 5*a* a rear perspective view of a wraparound hand splint according to an embodiment of the present invention is represented. The wraparound hand splint (500) having a front surface (502), contacting the patient's hand, and a back surface (504) adapted to affixed with the quick release fitting of the engagement member (not shown). The wraparound hand splint (500) includes a support frame (506), shown in FIG. 5*b*, having a longitudinal member (508) aligned with the axis of the patient's forearm and a transverse member (510) that wraps around the patient's wrist. Further, the support frame having a base panel (512) onto which a stud (400) is affixed by using a plurality of rivets (514). Finally, the support frame (506) is wrapped in a soft material (518) to provide the wraparound hand splint (500) so that the back surface (504) of the wraparound hand splint (500) is provided with a stud (400) to affix with the quick release fitting (not shown). In one embodiment, the support frame includes at least a horizontal member that is made of a malleable aluminum material that provides rigid support along one axis yet allows the horizontal member to be wrapped around the patient's wrist for support. Similarly, both the horizontal and vertical members may be such a malleable material. Alternatively the support frame can be made of an industry driven material known to a person of ordinary skill in the art.

Figure 5D:
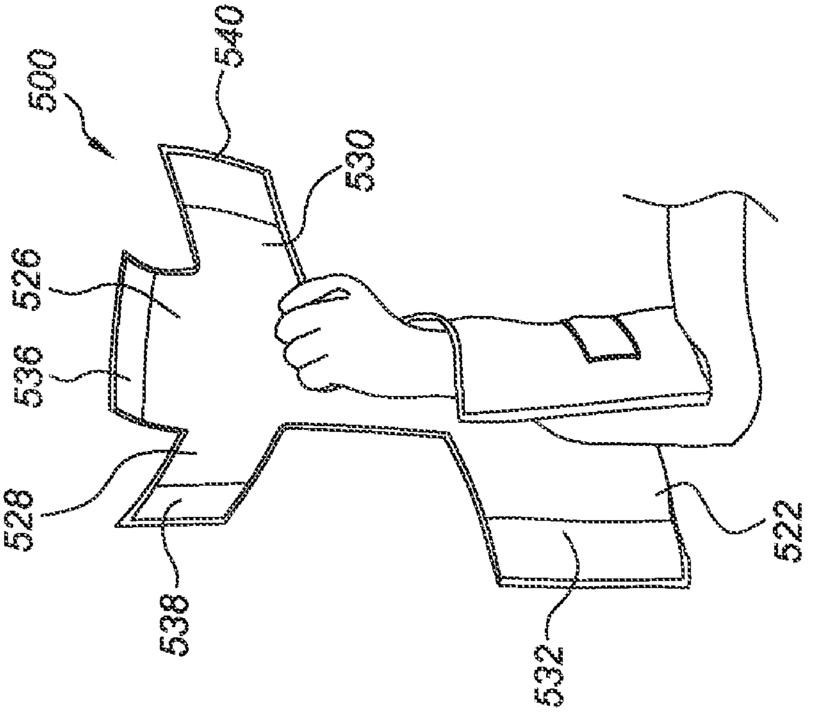
FIGS. 5*d* to 5*g* illustrate steps for applying the wraparound hand splint of FIGS. 5*a*-5*b* on a patient's hand.
Figure 5C:
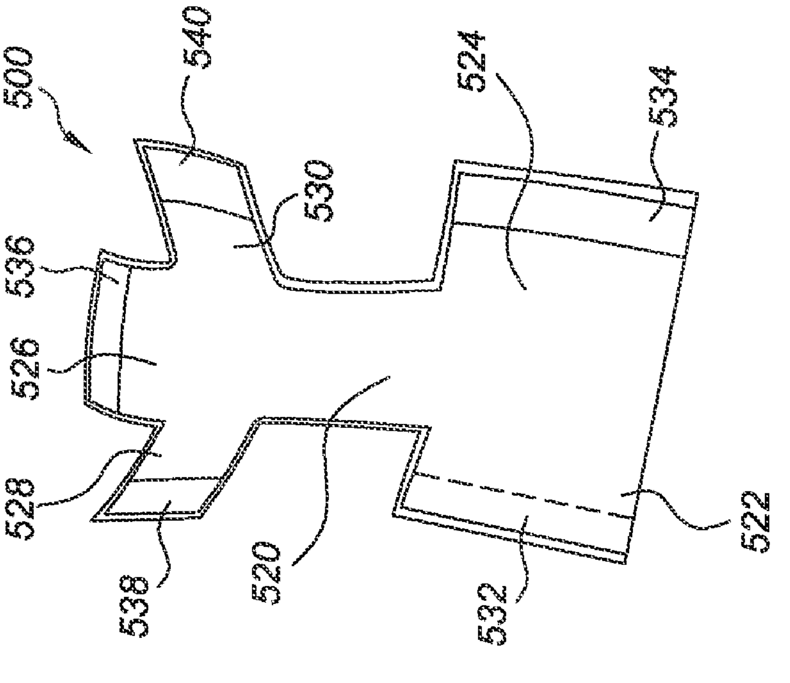
FIG. 5*c* illustrates a front view of the wraparound hand splint of FIG. 5*a;*

Referring to FIG. 5*c*, a front view of the wraparound hand splint of the FIG. 5*a* is represented. The wraparound hand splint (500) includes a central member (520) and first (522), second (524), third (526), fourth (528) and fifth panel (530) members extending outward from the central member (520). Each of the panels is provided with a fastener on their distal ends to wrap the panel around the patient's hand. Further, the third, fourth and fifth panels are provided with the fastener on the patient's hand contacting surface and the fastener on the first and the second panels are complementary to each other. In an embodiment, the distal end of the first panel (522) is provided with a fastener (532) on the patient contacting surface (502), and the distal end of the second panel (524) is provided with a fastener (534) on the back surface (504) of the wraparound hand splint (500). The distal end of the third, fourth, and fifth panels are provided with the fastener (536, 538, 540) respectively. Alternatively, position of the fasteners on the first and second panels can be reversed, i.e., the fastener on the second panel can be provided on the patient's contacting surface and the fastener on the first panel can be on the back surface.

Figure 5G:
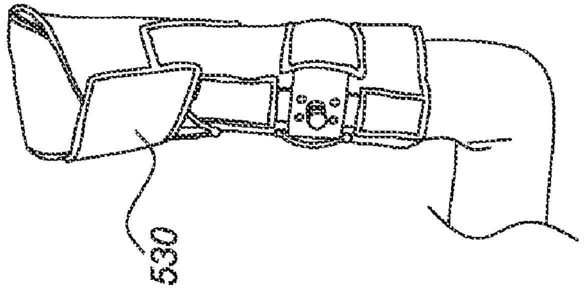
Figure 5F:
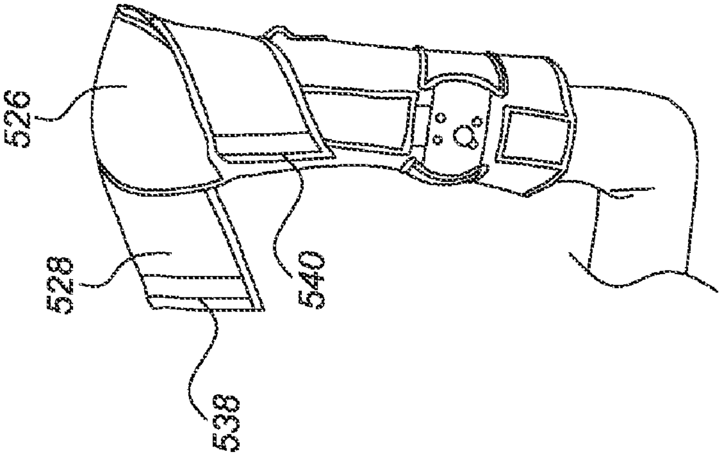
Figure 5E:
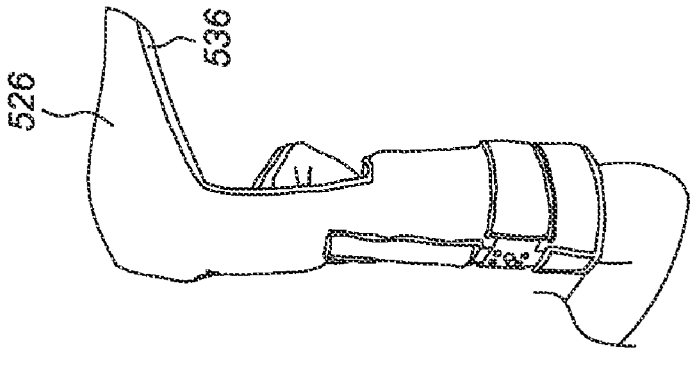

FIGS. 5*d*-5*g*, illustrate steps for applying the wraparound hand splint of the FIG. 5*c* on a patient's hand. As shown in FIG. 5*d*, first the volar side of the patient's hand in a relaxed fist position is laid on the central member (520) of the wraparound hand splint (500). The patient's hand is positioned such that the forearm of the patient is substantially coterminous with the central member (520). The first panel (522) is then folded around the wrist and the second panel (524) is then folded over the first panel (522) so that the fastener (532) on the first panel (522) is conformed to engage with the fastener (534) of second panel (524), shown in FIG. 5*e*. Following the engagement of the first (522) and second panel (524), the top panel (526) is disposed over the patient's hand in a relaxed fist position (FIG. 5*f*). Subsequently, the fourth (528) and fifth (530) panels are wrapped around the wrist of the patient's hand (FIG. 5*g*).

Figure 6A:
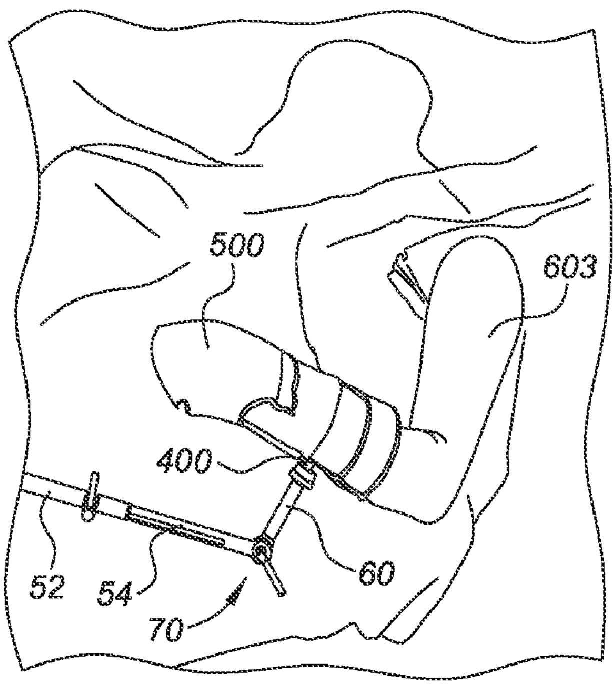
FIGS. 6*a*-6*d* illustrate a partial view of the arm support assembly of the present invention configured to position the patient's arm in different positions during the surgical procedure.
Figure 6B:
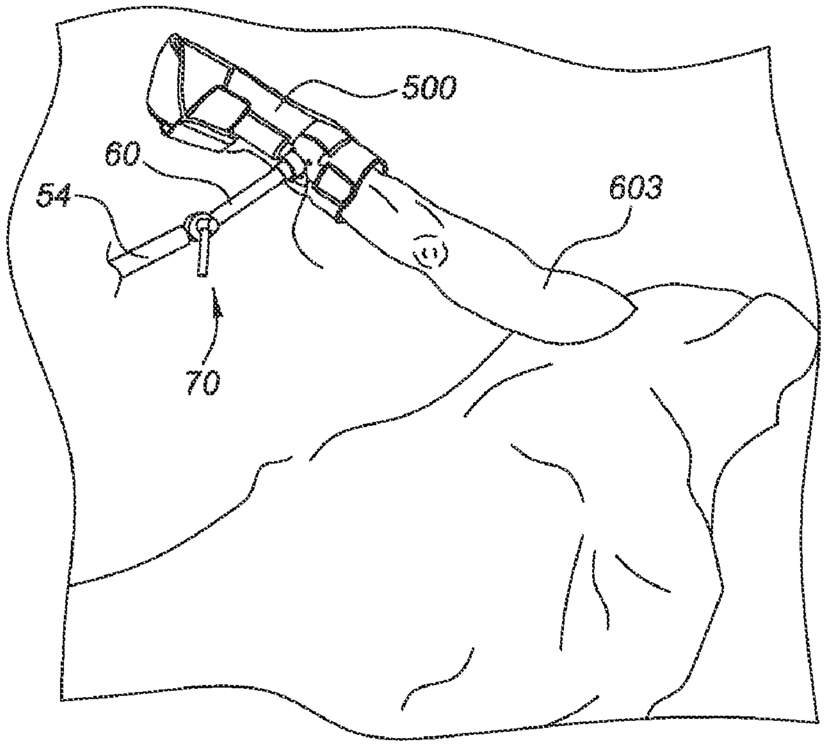
Figure 6C:
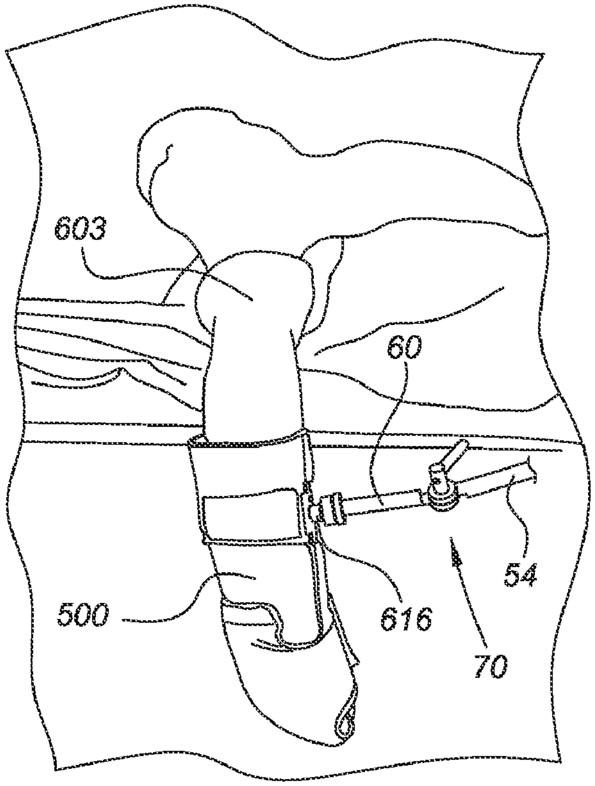
Figure 6D:
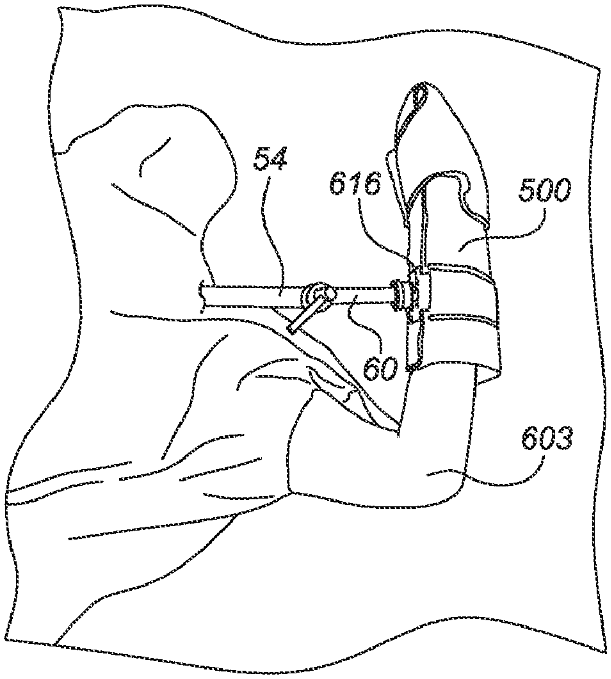

Referring to FIGS. 6*a-d*, illustrates a partial view of the arm support assembly of the present invention configured to position with the wraparound hand splint in different positions. The arm support assembly of the present invention can be configured to attain various surgical positions. The wraparound hand splint (500) is wrapped on a patient's arm (603) and finally attached to the engagement member (60) using the stud (400). FIG. 6*a* shows the patient's undergoing surgical procedure in a shoulder-beach chair position. Further, FIG. 6*b*, 6*c*, and 6*d* illustrate the patient in a shoulder-lateral decubitus position, elbow-lateral decubitus, and elbow-supine position respectively.

Various other embodiments are possible within the spirit of the invention and the aforementioned examples and embodiments are just meant to be for explanatory purposes, and in no way intend to limit the scope of the invention in any manner. The arm support assembly of the present invention can be made from various kinds of materials available in the field and known to a person skilled in the art. Preferably the arm support assembly of the present invention is made of material that can withstand the temperature and pressure conditions for autoclaving. The invention intends to cover all the equivalent embodiments and is limited only by the appended claims.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. An arm support assembly for supporting a patient's arm relative to a clamp support assembly disposed on an operating table accessory rail in a desired position during surgery comprising:

- a vertical member extending upwardly from the clamp support assembly;
- a horizontal member having first end and a second end, a length of the horizontal member being adjustable;
- a ball joint assembly connecting said horizontal member to the vertical member, said ball joint assembly comprising:
  - a socket portion having an opening configured to receive the vertical member that provides both rotational and vertical adjustment of said horizontal member relative to said vertical member; and
  - a ball clamp portion directly connected to said socket portion, the ball clamp portion providing independent angular adjustment of said horizontal member relative to said vertical member; and
- an engagement member having one end engaged with the second end of the horizontal member and other end having a fitting to receive a hand mitt.

2. The arm support assembly of claim 1, the ball clamp portion of the ball joint assembly comprising:

- a ball joint having a ball shaped end and an elongated end to engage the horizontal member;
- a first plate having an aperture to receive the elongated end therethrough;

a second plate having one surface to position the ball shape end and an opposite surface the first and second plates pivotally connected along adjoining sides thereof;

a clamping mechanism joining the first and second plates opposite said pivotal connection, wherein the ball shaped end is disposed between the first plate and the second plate and tightening of the clamping mechanism prevents movement of the horizontal member relative to the ball joint assembly.

3. The arm support assembly as claimed in claim 2, said clamping mechanism further comprising:

an actuator that engages a threaded screw wherein rotation of the actuator clamps the first plate and the second plate relative to one another; and a spherical washer positioned about the screw.

4. The arm support assembly as claimed in claim 2, further comprising:

a spring-biased retaining pin engaging hinges formed in said vertical member; and a locking knob, said locking knob engaging pin holds formed in the hinges to prevent accidental rotation of the horizontal member around the vertical member.

5. The arm support assembly as claimed in claim 1, wherein the hand mitt is a wraparound hand mitt.

6. The arm support assembly as claimed in claim 1, the horizontal member further comprising:

an articulated joint to allow selective angular adjustment of the engagement member.

7. The arm support assembly as claimed in claim 6, wherein the articulated joint is a wedge lock.

8. The arm support assembly as claimed in claim 1, wherein the fitting of the engagement member is connected to a stud protruding from the hand mitt.

9. The arm support assembly as claimed in claim 1, wherein the fitting of the engagement member is connected to a forearm pad adapted to support a patient's forearm.

10. The arm support assembly as claimed in claim 1, wherein the horizontal member is formed from a shaft member and a tube member, wherein the length of the horizontal member is telescopically adjusted by sliding the shaft member within the tube member.

11. The arm support assembly as claimed in claim 10, wherein the shaft member includes a groove to prevent rotation of the shaft member relative to the tube member.

12. The arm support assembly as claimed in claim 10, further comprising a safety knob to engage the shaft member relative to the tube member.

* * * * *